United States Patent [19]

Louderback

[11] 4,288,343

[45] * Sep. 8, 1981

[54] METHOD FOR INCREASING SHELF-LIFE OF A SERUM BILIRUBIN REFERENCE COMPOSITION AND COMPOSITION PRODUCED THEREBY

[75] Inventor: Allan L. Louderback, Temple City, Calif.

[73] Assignee: Beckman Instruments, Inc., Fullerton, Calif.

[ * ] Notice: The portion of the term of this patent subsequent to May 6, 1997, has been disclaimed.

[21] Appl. No.: 22,567

[22] Filed: Mar. 22, 1979

Related U.S. Application Data

[63] Continuation-in-part of Ser. No. 925,484, Jul. 17, 1978, Pat. No. 4,201,694.

[51] Int. Cl.$^3$ .................. G01N 33/48; C09K 3/00
[52] U.S. Cl. .................... 252/408; 23/230 B; 23/905; 422/61; 424/2; 424/3; 435/4; 435/4; 422/61
[58] Field of Search ............. 252/408; 23/230 B, 905; 424/2, 3

[56] References Cited

U.S. PATENT DOCUMENTS

| | | | |
|---|---|---|---|
| 3,873,269 | 3/1975 | Kraffczyk et al. | 252/408 |
| 3,876,375 | 4/1975 | Maurukas | 252/408 |
| 4,030,885 | 6/1977 | Das | 252/408 |
| 4,090,977 | 5/1978 | Dudin | 252/408 |
| 4,121,905 | 10/1978 | Maurukas | 252/408 |
| 4,189,401 | 2/1980 | Louderback | 252/408 |
| 4,201,694 | 5/1980 | Louderback | 252/408 |

OTHER PUBLICATIONS

Zebelman, A. M., et al., Clin. Chem., vol. 22, No. 6, pp. 934–935 (1976).
Doumas, B. T., et al., Clin. Chem., vol. 19, No. 9, pp. 984–993 (1973).
Billing, B. H., et al., Biochem. J., vol. 65, pp. 774–784 (1957).
Henry, R. J., "Clinical Chemistry", Hoeber Med. Div., Harper & Row, N. Y., N. Y., pp. 571–617 (1972).
Michaelsson, M., Scand. J. Clin. Lab. Invest., vol. 13, Suppl. 56, pp. 1–80 (1961).
NBS Std. Ref. Material 916, "Bilirubin" (1971).
Andrews, A. T., et al., Arch. Biochem. Biophys., vol. 141, pp. 538–546 (1970).
Joint Committee Report, "Recommendation on a Uniform Bilirubin Standard", Clin. Chem., vol. 8, No. 4, pp. 405–407 (1961).
Tietz, N. W., "Clinical Chemistry", W. B. Saunders Co., Phila., Pa., 2nd Ed., pp. 1035–1040 (1976).

*Primary Examiner*—Teddy S. Gron
*Attorney, Agent, or Firm*—R. J. Steinmeyer; J. E. Vanderburgh; R. S. Frieman

[57] ABSTRACT

A stable blood serum bilirubin reference composition characterized in that the composition possess a pH of from about 8.2 to about 9.2 and comprises (a) a sulfhydryl compound in an amount sufficient to enhance the stability of the bilirubin and (b) a chelating agent in an amount sufficient to bind all the metals present in the blood serum moiety of the composition. This blood serum bilirubin composition when stored in a gas impervious vial under an inert atmosphere has an excellent shelf life.

14 Claims, No Drawings

METHOD FOR INCREASING SHELF-LIFE OF A SERUM BILIRUBIN REFERENCE COMPOSITION AND COMPOSITION PRODUCED THEREBY

CROSS-REFERENCE TO RELATED APPLICATION

This application is a continuation-in-part of copending application Ser. No. 925,484, filed July 17, 1978 now U.S. Pat. No. 4,201,694.

BACKGROUND OF THE INVENTION

1. Field of the Invention

This invention relates to a laboratory material and, more particularly, to a stable blood serum bilirubin referencce composition.

2. Description of the Prior Art

A concentration of bilirubin of 20 milligram per 100 milliliter (20 mg%) is used as a criteria by physicans for determining at which point one must transfuse a newborn infant so that there is no brain damage. This procedure usually occurs with newborn infants who undergo considerable trauma during the birth process. The newborn will either be transfused or blood exchanged on the basis of a bilirubin test.

At present, controls are made by a lyophilization process to stabilize various analytes including bilirubin. These lyophilized controls must be reconstituted by the clinical laboratory before use. The reconstituted controls are only useful as a calibrator for a maximum period of about one day. The reconstituted control slowly breaks down to lower and lower values. However, the clinical laboratory is always using the calibrator's theoretically high value which, unfortunately, can lead to erroneous results.

Prior art bilirubin reference standards have been reported to deteriorate about 2% per month when stored at $-23°$ C. This deterioration prohibits long storage at this temperaure. Bilirubin reference standards stored at 31 16° C. for twelve days exhibit about a 5% deterioration at the end of this period. At $-70°$ C., bilirubin standards exhibited relatively good stability, deteriorating about 1% in six months. Tietz, *Fundamentals of Clinical Chemistry*, W. B. Saunders Company, Philadelphia, Penn., 2nd Edition (1976), 1035–1043, and Doumas et al., Clinical Chemistry, 19 (9):984 (1973), said publications being incorporated herein in toto by reference.

SUMMARY OF THE INVENTION

The instant invention encompasses a blood serum bilirubin reference composition having an improved shelf life. The blood serum bilirubin reference composition is characterized in that the composition possesses a pH of about 8.2 to about 9.2 and further comprises (a) a sulfhydryl compound in an amount sufficient to enhance the stability of bilirubin and (b) a chelating agent in an amount sufficient to bind all the metals present in the blood serum moiety of the composition. Furthermore, it is desirable to store the blood serum reference composition of the present invention in a gas impervious container and, preferably, also under an inert atmosphere.

DESCRIPTION OF THE PREFERRED EMBODIMENTS

The improved blood serum reference composition of the instant invention is of the type comprising blood serum having a bilirubin constituent of a known value. In accordance with the invention, the improved blood serum reference composition is characterized in that the composition possesses a pH of from about 8.2 to about 9.2, preferably, from about 8.4 to about 8.9, and more preferably about 8.7. The pH of the blood serum reference composition of the instant invention is outside the pH range of 7.3 to 7.4 which the prior art taught to be essential for maximum stability of the bilirubin standard. See Tietz, supra.

The pH can be adjusted by any conventional means employed by those skilled in the art, e.g., by the addition of NaOH to the composition.

This invention's improved blood serum reference composition is also characterized in that the composition further comprises a sulfhydryl conpound in an amount sufficient to further enhance the stability of bilirubin.

The normal range of oxidation-reduction (REDOX) potential for plasma is from about $+7$ to about $+40$ millivolts depending upon the freshness of the plasma. It has been discovered that by reducing the REDOX potential of plasma with sulfhydryl compounds, one is able to greatly prolong the shelf life of a bilirubin composition. Although the exact amount of the sulfhydryl compound employed is not critical, one should avoid using too much sulfhydryl compound in order to avoid cross linking the sulfhydryl bonds. The cross-linking of sulfhydryl bonds forms a disulfide bridge (—S—S—) which results in a polymer matrix. This polymer matrix imparts a gel-like consistency to the composition thereby rendering it undesirable for clinical use. In a similar fashion, if too little sulfhydryl compound is employed, the bilirubin composition will not be stable. Therefore, sulfhydryl compounds should be employed in an amount sufficient to enhance the stability of bilirubin without imparting undesirable characteristics to the composition, said amount preferably being sufficient to reduce the REDOX potential of the composition to from about $-30$ to about $-300$ millivolts. More preferably the sulfhydryl compounds are employed in an amount sufficient to reduce the REDOX potential to from about $-100$ to about $-200$ millivolts. Optimally the amount of sulfhydryl compounds employed is such that the REDOX potential is reduced to about $-160$ millivolts.

Any of the numerous sulfhydryl compounds known to those skilled in the art can be employed as a reducing agent in the instant invention. For example, the sulfhydryl compound can be selected from a group consisting of dithioerythreitol, dithiothreitol (DTE), mercaptoethanol, cysteine, reduced gluthathione, N-acetyl cysteine, mercaptoacetate, as well as mixtures thereof. Preferably, the sulfhydryl compound is DTE.

In addition to the above, this invention's improved blood serum reference composition is also further characterized in that the composition further comprises a chelating agent in an amount sufficient to bind all the metals present in the blood serum moiety of the composition. Although the exact amount of chelating agent employed is not critical, from about 25 to about 1,000, preferably from about 5 to about 150, and more preferably about 100 mg of chelating agent is used per 100 ml of blood serum reference composition of the instant invention.

Essentially any chelating agent can be used in the composition of the present invention. Known chelating agents are discussed in Flaschka et al., Chelates in Analyical Chemistry, Volumes I-V, Marcel Decker, Inc., New York, N.Y., said publication being incorporated herein in toto by reference. Typical chelating agents include ethylenediaminetetraacetic acid (EDTA), nitrolotriacetic acid, ethylenediamino, diethylenetriamine, triethyltetramine, tetraethylenepentamine, pentaethylenehexamine, N-hydroxyethyliminodiacetic acid, N-hydroxyethyl-N,N',N', ethylenediaminitriacetic acid, N,N,N'N'',N''-diethylenetriaminepentaacetic acid, citric acid, tartanic acid, gluconic acid, tripolyphosphate ion, polyphosphate anion, N,N'-ethylenebis[2-(o-hydroxypnehyl] glycine, 3,5-disulfopyrocatechol, bis(orthohydroxybenzyl)ethylenediamine-N,N'-diacetic acid, salts thereof, and mixtures thereof. Preferably the chelating agent selected from the group consisting of EDTA, salts thereof and mixtures. More preferably, the chelating agent is EDTA disodium salt. Other salts of EDTA include the sodium potassium salt and the tetrasodium salt thereof.

Although any blood serum reference composition of the type comprising blood serum having a bilirubin constituent of a known value can be employed in the present invention, it is preferred to employ a bilirubin reference composition comprising in its non-biological component from about 60 to about 80, more preferably from about 66 to about 70, weight percent water, from about 20 to about 40, more preferably from about 30 to about 34, weight percent of at least one alkylene polyol having from 2-5 carbon atoms, the remainder being bilirubin and, optionally, other natural biological materials selected from a group consisting of blood serum, enzymes, metabolites, electrolytes, and hormones. This matrix is described in detail in U.S. Pat. No. 3,876,375, said publication being incorporated herein in toto by reference.

The blood serum reference composition of the present invention preferably is stored in a gas impervious container, such as a glass ampule, under an inert gas atmosphere, such as nitrogen, argon, or helium. Preferably, the container is also impervious to visible light.

The stable blood serum bilirubin reference composition of the instant invention can be employed as a blood serum bilirubin reference standard or as a blood serum bilirubin reference control, i.e., the composition can be employed to either calibrate an instrument or can be employed to periodically verify that the instrument is still operating within the tolerances desired. For the above uses, the blood serum bilirubin reference composition of the instant invention can contain known amounts of bilirubin of from about 0.1 to about 40 milligrams per deciliter (mg/dl). Other ranges of bilirubin of use to the clinical chemist include ranges from about 1 to about 30 mg/dl and also from about 2 to about 25 mg/dl.

The following examples are provided for the purpose of further illustration only and are not intended to be limitations on the disclosed invention.

EXAMPLES 1-9

A bilirubin composition comprising 20 mg/dl bilirubin; 15 mg/dl DTE, and 100 mg/dl EDTA disodium salt in a solution comprising about 66⅔ weight percent water and about 33⅓ weight percent ethylene glycol and having a pH of from 7.0 to 9.0 were formulated and stored in vials. These vials were incubated at various temperatures ($-15°$ C., $32°$ C., $37°$ C., and $41°$ C.) and assayed at designated time intervals. The data obtained from the experiments are set forth in Tables I-IX. Table X sets forth a summary of the Arrhenius plot for 90% life based on data obtained at 41, 37, and $32°$ C.

TABLE I

| | | | pH 7.0 | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 15.8 | 100 | 15.8 | 100 | 15.8 | 100 | 15.8 |
| 24.0 | 14.6 | 92 | 15.0 | 95 | 14.9 | 94 | 15.8 |
| 72.0 | 11.1 | 74 | 12.0 | 80 | 14.0 | 93 | 15.0 |
| 96.0 | 10.0 | 62 | 12.4 | 77 | 14.4 | 90 | 16.0 |
| 120.0 | 8.0 | 50 | 12.0 | 75 | 14.0 | 87 | 16.0 |
| 168.0 | N/A[1] | | 9.1 | 54 | 13.0 | 76 | 17.0 |
| 336.0 | N/A | | 4.4 | 27 | 10.1 | 63 | 16.0 |
| 504.0 | N/A | | N/A | | 7.1 | 44 | 16.1 |

[1]N/A denotes not available.

TABLE II

| | | | pH 7.3 | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 16.1 | 100 | 16.1 | 100 | 16.1 | 100 | 16.1 |
| 24.0 | 15.3 | 95 | 15.7 | 98 | 15.1 | 94 | 16.1 |
| 48.0 | 14.5 | 90 | 15.4 | 96 | 15.8 | 98 | 16.1 |
| 72.0 | 12.1 | 79 | 14.0 | 92 | 14.4 | 94 | 16.0 |
| 96.0 | 11.1 | 69 | 14.0 | 87 | 15.0 | 94 | 16.0 |
| 120.0 | 8.2 | 50 | 12.0 | 78 | 14.1 | 86 | 16.4 |
| 168.0 | N/A[1] | | 10.3 | 60 | 14.0 | 82 | 17.1 |
| 336.0 | N/A | | 5.0 | 31 | 11.3 | 71 | 16.0 |
| 504.0 | N/A | | N/A | | 8.6 | 52 | 16.4 |

[1]N/A denotes not available.

TABLE III

| | | pH 7.6 | | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 16.4 | 100 | 16.4 | 100 | 16.4 | 100 | 16.4 |
| 24.0 | 15.3 | 93 | 15.9 | 97 | 16.1 | 98 | 16.4 |
| 48.0 | 15.5 | 94 | 15.8 | 96 | 16.9 | 102 | 16.5 |
| 72.0 | 13.1 | 82 | 15.0 | 94 | 15.0 | 94 | 15.9 |
| 96.0 | 12.4 | 77 | 14.2 | 88 | 15.2 | 94 | 16.1 |
| 120.0 | 10.0 | 61 | 13.0 | 80 | 15.1 | 93 | 16.3 |
| 168.0 | 9.0 | 53 | 12.0 | 71 | 14.6 | 86 | 17.0 |
| 336.0 | 4.2 | 26 | 6.4 | 40 | 12.4 | 77 | 16.2 |
| 504.0 | | N/A[1] | | N/A | 10.3 | 60 | 16.2 |

[1]N/A denotes not available.

TABLE IV

| | | pH 8.0 | | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 17.2 | 100 | 17.2 | 100 | 17.2 | 100 | 17.2 |
| 24.0 | 61.3 | 95 | 16.6 | 97 | 16.8 | 98 | 17.2 |
| 48.0 | 15.7 | 92 | 16.8 | 99 | 17.5 | 103 | 17.0 |
| 72.0 | 14.0 | 87 | 15.0 | 94 | 15.1 | 94 | 16.0 |
| 96.0 | 14.0 | 82 | 15.0 | 88 | 16.0 | 94 | 17.0 |
| 120.0 | 12.1 | 71 | 15.2 | 89 | 15.4 | 91 | 17.0 |
| 168.0 | 11.0 | 64 | 13.1 | 76 | 15.3 | 89 | 17.2 |
| 336.0 | 6.2 | 36 | 8.0 | 47 | 13.3 | 78 | 17.0 |
| 504.0 | | N/A[1] | | N/A | 11.2 | 65 | 17.1 |

[1]N/A denotes not available.

TABLE V

| | | pH 8.2 | | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 17.3 | 100 | 17.3 | 100 | 17.3 | 100 | 17.3 |
| 24.0 | 16.6 | 96 | 16.8 | 97 | 17.0 | 98 | 17.3 |
| 48.0 | 16.0 | 91 | 16.9 | 97 | 17.3 | 99 | 17.5 |
| 72.0 | 14.1 | 87 | 15.1 | 98 | 15.1 | 98 | 16.3 |
| 120.0 | 12.2 | 72 | 15.3 | 90 | 16.0 | 94 | 17.0 |
| 168.0 | 11.2 | 63 | 14.0 | 79 | 15.4 | 87 | 17.7 |
| 336.0 | 6.0 | 35 | 9.0 | 53 | 14.0 | 82 | 17.0 |
| 504.0 | | N/A[1] | 5.5 | 32 | 11.8 | 69 | 17.2 |

[1]N/A denotes not available.

TABLE VI

| | | pH 8.4 | | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 17.4 | 100 | 17.4 | 100 | 17.4 | 100 | 17.4 |
| 24.0 | 16.8 | 97 | 16.8 | 97 | 16.7 | 96 | 17.4 |
| 48.0 | 16.2 | 92 | 17.2 | 98 | 17.6 | 100 | 17.6 |
| 72.0 | 15.1 | 89 | 15.1 | 89 | 15.2 | 89 | 17.0 |
| 96.0 | 14.0 | 73 | 14.3 | 84 | 16.1 | 95 | 17.0 |
| 120.0 | 12.4 | 73 | 14.3 | 84 | 16.1 | 95 | 17.0 |
| 168.0 | 12.0 | 67 | 14.0 | 78 | 15.6 | 87 | 18.0 |
| 336.0 | 6.0 | 35 | 8.2 | 48 | 14.0 | 82 | 17.1 |

TABLE VII

| | | pH 8.6 | | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 17.7 | 100 | 17.7 | 100 | 17.7 | 100 | 17.7 |
| 24.0 | 17.1 | 97 | 17.3 | 98 | 17.4 | 98 | 17.7 |
| 48.0 | 16.3 | 92 | 17.3 | 97 | 17.5 | 98 | 17.8 |
| 72.0 | 15.1 | 89 | 15.2 | 89 | 15.6 | 92 | 17.0 |
| 96.0 | 14.4 | 84 | 16.1 | 94 | 16.8 | 98 | 17.1 |

TABLE VII-continued

| | pH 8.6 | | | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 120.0 | 12.2 | 71 | 14.4 | 83 | 16.1 | 93 | 17.3 |
| 168.0 | 12.0 | 66 | 14.1 | 78 | 16.1 | 89 | 18.1 |
| 336.0 | 5.3 | 30 | 8.2 | 47 | 14.0 | 80 | 17.5 |
| 504.0 | N/A[1] | | N/A | | 11.1 | 62 | 17.8 |

[1]N/A denotes not available.

TABLE VIII

| | pH 8.8 | | | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 17.7 | 100 | 17.7 | 100 | 17.7 | 100 | 17.7 |
| 24.0 | 17.1 | 97 | 17.2 | 97 | 17.5 | 99 | 17.7 |
| 48.0 | 15.9 | 88 | 17.5 | 97 | 17.7 | 98 | 18.1 |
| 72.0 | 15.1 | 89 | 15.3 | 90 | 15.8 | 93 | 17.0 |
| 96.0 | 14.5 | 81 | 16.1 | 89 | 16.8 | 93 | 18.0 |
| 120.0 | 12.0 | 69 | 14.2 | ·82 | 16.1 | 93 | 17.4 |
| 168.0 | 11.5 | 62 | 13.3 | 72 | 16.0 | 86 | 18.5 |
| 336.0 | 4.3 | 24 | 7.1 | 40 | 14.1 | 80 | 17.6 |
| 504.0 | N/A[1] | | N/A | | 10.4 | 58 | 17.9 |

[1]N/A denotes not available.

TABLE IX

| | pH 9.0 | | | | | | |
|---|---|---|---|---|---|---|---|
| | 41° C. | | 37° C. | | 32° C. | | −15° C. |
| Hour | A | $\frac{A}{D} \times 100\%$ | B | $\frac{B}{D} \times 100\%$ | C | $\frac{C}{D} \times 100\%$ | D |
| 0.0 | 17.6 | 100 | 17.6 | 100 | 17.6 | 100 | 17.6 |
| 24.0 | 17.1 | 97 | 17.3 | 98 | 17.5 | 99 | 17.6 |
| 48.0 | 16.1 | 88 | 17.1 | 94 | 17.5 | 96 | 18.2 |
| 72.0 | 15.1 | 88 | 15.3 | 89 | 15.8 | 92 | 17.2 |
| 96.0 | 17.4 | 97 | 16.0 | 89 | 17.1 | 95 | 18.0 |
| 120.0 | 11.1 | 63 | 15.1 | 86 | 16.1 | 92 | 17.5 |
| 168.0 | 9.2 | 50 | 13.1 | 71 | 16.1 | 87 | 18.5 |
| 336.0 | N/A[1] | | 6.0 | 33 | 13.0 | 72 | 18.0 |
| 504.0 | N/A | | N/A | | 9.1 | 51 | 18.0 |

[1]N/A denotes not available.

TABLE X

| Temperature | ARRHENIUS PLOT FOR 90% LIFE BASED ON TEMPERATURES 41°, 37°, AND 32° C. | | | | | | | | |
|---|---|---|---|---|---|---|---|---|---|
| °C. | 7.0 | 7.3 | 7.6 | 8.0 | 8.2 | 8.4 | 8.6 | 8.8 | 9.0 |
| 4 | 8.16M[1] | 1.80Y | 1.87Y | 1.39Y | 3.30Y | 7.95Y | 1.91Y | 2.03Y | 5.94M |
| −15 | 26.11Y[2] | 124.34Y | 112.46Y | 57.86Y | 242.74Y | 1024.42Y | 104.41Y | 128.60Y | 12.80Y |

[1]M denotes months.
[2]Y denotes years.

The data set forth in Tables I–X demonstrate that the serum bilirubin reference compositions within the scope of the instant invention are stable for periods of time far exceeding the shelf life of prior art serum bilirubin reference compositions.

Based on this disclosure, many other modifications and ramifications will naturally suggest themselves to those skilled in the art. These are intended to be comprehended as within the scope of this invention.

The embodiments of the invention in which an exclusive property or priviledge is claimed are defined as follows:

1. An improved blood serum reference composition of the type comprising blood serum having a bilirubin constituent of known value, characterized in that said composition possesses a pH of from about 8.2 to about 9.2 and further comprises:

(a) a sulfhydryl compound in an amount sufficient to further enhance the stability of bilirubin and
(b) a chelating agent in an amount sufficient to bind the metals present in said blood serum.

2. The composition of claim 1 wherein said sulfhydryl compound is present in an amount such that the oxidation-reduction potential of said composition is from about −30 to about −300 millivolts and wherein said composition comprises from about 25 to about 1,000 mg chelating agent per 100 ml serum.

3. The composition of claim 1 wherein said sulfhydryl compound is present in an amount such that the oxidation-reduction potential of said composition is from about −100 to about −200 millivolts, wherein said composition comprises from about 50 to about 150 mg chelating agent per 100 ml serum, and wherein said composition possesses a pH of from about 8.4 to about 8.9.

4. The composition of claim 3 wherein said sulfhydryl compound is present in an amount such that the oxidation-reduction potential of said composition is about −160 millivolts, wherein said composition comprises about 100 mg chelating agent per 100 ml serum, and wherein said composition possesses a pH of about 8.7.

5. The composition of claim 4 wherein said sulfhydryl compound is selected from a group consisting of dithioerythreitol, dithiothreitol, mercaptrethanol, cysteine, reduced gluthione, N-acetyl cysteine, mercaptoacetate, and mixtures thereof, and wherein said chelating agent is selected from a group consisting of ethylenediaminetetraacetic acid, nitrilotriacetic acid, ethylenediamino, diethylenetriamine, triethyltetramine, tetraethylenepentamine, pentaethylenehexamine, N-hydroxyethyliminodiacetic acid, N-hydroxyethyl-N,N',N', ethylenediaminitriacetic acid, N,N,N',N'',N''-diethylenetriaminepentaacetic acid, citric acid, tartanic acid, gluconic acid, tripolyphosphate ion, polyphosphate anion, N,N'-ethylenebis[2-(o-hydroxyphenyl]glycine, 3,5-disulfopyrocatechol, bis-(orthohydroxybenzyl)ethylenediamine-N,N'-diacetic acid, salts thereof, and mixtures thereof.

6. The composition of claim 5 wherein said sulfhydryl compound is dithiothreitol and wherein said chelating agent is selected from the group consisting of ethylenediaminetetraacetic acid, salts thereof, and mixtures thereof.

7. An improved bilirubin reference composition comprising in its non-biological component from about 60 to about 80 weight percent water, from about 20 to about 40 weight percent of at least one alkylene polyol having from 2 to 5 carbon atoms, the remainder being bilirubin and, optionally, other natural biological materials selected from a group consisting of blood serum, enzymes, metabolites, electrolytes, and hormones, characterized in that said composition possesses a pH of from about 8.2 to about 9.2 and further comprises:

(a) a sulfhydryl compound in an amount sufficient to further enhance the stability of bilirubin and (b) a chelating agent in an amount sufficient to bind the metals present in said blood serum.

8. The composition of claim 7 wherein said sulfhydryl compound is present in an amount such that the oxidation-reduction potential of said composition is from about −30 to about −300 millivolts and wherein said composition comprises from about 25 to about 1,000 mg chelating agent per 100 ml serum.

9. The composition of claim 7 wherein said sulfhydryl compound is present in an amount such that the oxidation-reduction potential of said composition is from about −100 to about −200 millivolts, wherein composition comprises from about 50 to about 150 mg chelating agent per 100 ml serum, and wherein said composition possesses a pH of from about 8.4 to about 8.9.

10. The composition of claim 9 wherein said sulfhydryl compound is present in an amount such that the oxidation-reduction potential of said composition is about −160 millivotls, wherein said composition comprises about 100 mg chelaying agent per 100 ml serum, and wherein said composition possesses a pH of about 8.7.

11. The composition of claim 10 wherein said sulfhydryl compound is selected from a group consisting of dithioerythritol, dithiothreitol, mercaptrethanol, cysteine, reduced gluthione, N-acetyl cysteine, mercaptoacetate, and mixtures thereof, and wherein said chelating agent is selected from a group consisting of ethylenediaminetetraacetic acid, nitrilotriacetic acid, ethylenediamino, diethylenetriamine, triethyltetramine, tetraethylenepentamine, pentaethylenehexamine, N-hydroxyethyliminodiacetic acid, N-hydroxyethyl-N,N',N',ethylenediamietriacetic acid, N,N,N',N'',N''-diethylenetriaminepentaacetic acid, citric acid, tartanic acid, gluconic acid, tripolyphosphate ion, polyphosphate anion, N,N'-ethylenebis[2-(o-hydroxyphenyl]glycine, 3,5-disulfopyrocatechol, bis-(orthohydroxybenzyl)ethylenediamine-N,N'-diacetic acid, salts thereof, and mixtures thereof.

12. The composition of claim 7 wherein said sulfhydryl compound is dithiothreitol and wherein said chelating agent is selected from the group consisting of ethylenediaminetetraacetic acid, salts thereof, and mixtures thereof.

13. An article comprising a gas impervious container having located therein an inert gas and the composition of any one of claims 1–11 or 12.

14. An article comprising a gas impervious container which is also impervious to visible light and having located therein an inert gas and the composition of any one of claims 1–11 or 12.

* * * * *